United States Patent
Baek (10) Patent No.: US 7,770,436 B2
(45) Date of Patent: Aug. 10, 2010

(54) MICRO RHEOMETER FOR MEASURING FLOW VISCOSITY AND ELASTICITY FOR MICRON SAMPLE VOLUMES

(75) Inventor: Seong-Gi Baek, Pleasanton, CA (US)

(73) Assignee: Rheosense, Inc., San Ramon, CA (US)

( * ) Notice: Subject to any disclaimer, the term of this patent is extended or adjusted under 35 U.S.C. 154(b) by 35 days.

(21) Appl. No.: 11/983,210

(22) Filed: Nov. 6, 2007

(65) Prior Publication Data
US 2008/0134765 A1    Jun. 12, 2008

Related U.S. Application Data

(63) Continuation-in-part of application No. 11/078,015, filed on Mar. 11, 2005, now Pat. No. 7,290,441, which is a continuation-in-part of application No. 10/286,602, filed on Oct. 31, 2002, now Pat. No. 6,892,583, said application No. 11/078,015.

(60) Provisional application No. 60/335,375, filed on Oct. 31, 2001, provisional application No. 60/552,289, filed on Mar. 11, 2004.

(51) Int. Cl.
*G01N 11/08* (2006.01)
*G01N 21/00* (2006.01)

(52) U.S. Cl. .................... 73/54.09; 73/54.16; 73/54.43; 73/54.39

(58) Field of Classification Search ................ 73/54.01, 73/54.04, 54.09
See application file for complete search history.

(56) References Cited

U.S. PATENT DOCUMENTS 4,241,602 A    12/1980    Han et al.

(Continued)

FOREIGN PATENT DOCUMENTS

JP    6-201420    7/1991

(Continued)

OTHER PUBLICATIONS

Rodd, L. E., Scott, T. P., Boger, D. V., Cooper-White, J. J. and McKinley, G. H., "Planar Entry Flow of Low Viscosity Elastic Fluids in Micro-Fabricated Geometries." J. Non-Newt. Fluid Mech. 129. 2005. pp. 1-22.*

(Continued)

*Primary Examiner*—Lisa M Caputo
*Assistant Examiner*—Punam Roy
(74) *Attorney, Agent, or Firm*—Thorpe North & Western LLP (57) ABSTRACT

A micro-rheometer for measuring flow characteristics such as viscosity, elasticity, and flow rate of a sample liquid combines well defined micro-fabricated flow channels having geometry changes forming a constriction region therein to a monolithically fabricated pressure sensor arrays. The pressure sensor array positions pressure sensors to measure the viscosity of the sample liquid while flowing in a uniform length of the flow passage and to measure the extensional viscosity while flowing through the constriction region of the passage. The invention can improve the measurement accuracy of the flow rate, viscosities, or elasticities over a wide range of shear rate. The accuracy of the viscosity over a broader range of shear rate or flow rate measurement over broader range of flow rates can be accomplished by employing monolithically integrated pressure sensors fabricated with different sensitivities disposed in a known manner. The invention further includes necessary components such as a display, a pumping system, valve manifolds, and software for a portable or laboratory measurement instrument, process control, and high throughput measurements.

15 Claims, 8 Drawing Sheets

U.S. PATENT DOCUMENTS

| | | | |
|---|---|---|---|
| 4,874,500 A * | 10/1989 | Madou et al. | 204/412 |
| 4,894,698 A | 1/1990 | Hijikigawa et al. | |
| 5,029,479 A | 7/1991 | Bryan | |
| 5,165,292 A * | 11/1992 | Prohaska | 73/54.04 |
| 5,189,777 A | 3/1993 | Guckel et al. | |
| 5,304,487 A * | 4/1994 | Wilding et al. | 435/29 |
| 5,485,753 A | 1/1996 | Burns et al. | |
| 5,486,335 A * | 1/1996 | Wilding et al. | 422/55 |
| 5,602,339 A * | 2/1997 | Wareham | 73/730 |
| 5,756,883 A * | 5/1998 | Forbes | 73/54.05 |
| 5,983,727 A | 11/1999 | Wellman et al. | |
| 6,010,461 A * | 1/2000 | Haniff et al. | 600/561 |
| 6,032,689 A | 3/2000 | Tsai et al. | |
| 6,237,398 B1 * | 5/2001 | Porat et al. | 73/54.09 |
| 6,840,092 B2 * | 1/2005 | Eggen et al. | 73/54.11 |
| 6,892,583 B2 | 5/2005 | Baek | |
| 7,290,441 B2 | 11/2007 | Baek | |
| 2003/0079547 A1 | 5/2003 | Baek | |
| 2004/0037739 A1 * | 2/2004 | McNeely et al. | 422/58 |
| 2005/0183496 A1 | 8/2005 | Baek | |
| 2005/0210964 A1 | 9/2005 | Baek | |

FOREIGN PATENT DOCUMENTS

WO    WO 2005/086883    9/2005

OTHER PUBLICATIONS

Chien, R.-D., Jong, W.-R., and Chen, S.-C., "Study on rheological behavior of polymer melt flowing through micro-channels considering the wall-slip effect." J. Micromech. Microeng. 15. 2005. pp. 1389-1396.*

* cited by examiner

MICRO RHEOMETER FOR MEASURING FLOW VISCOSITY AND ELASTICITY FOR MICRON SAMPLE VOLUMES

RELATED APPLICATIONS

This application is a continuation-in-part of U.S. patent application Ser. No. 11/078,015, filed Mar. 11, 2005, and entitled "Micro Slit Viscometer With Monlithically Integrated Pressure Sensors", now U.S. Pat. No. 7,290,441, which was a continuation-in-part of U.S. patent application Ser. No. 10/286,602, filed Oct. 31, 2002, now U.S. Pat. No. 6,892,583, which claimed the benefit of provisional application Ser. No. 60/335,375, filed Oct. 31, 2001, both entitled "Pressure Sensing Device For Rheometers." application Ser. No. 11/078,015 also claimed the benefit of U.S. Provisional Patent Application Ser. No. 60/552,289, filed Mar. 11, 2004, and entitled "Micro Slit Viscometer with Monolithically Integrated Pressure Sensors." All of the above applications are incorporated herein by reference.

BACKGROUND OF INVENTION

1. Field

This invention is in the field of miniature rheometer or viscometer devices that measure true viscosity, elasticity, or flow rate of liquid.

2. State of the Art

Viscosity is a measure of resistance of liquid to flow and its value depends on the rate of deformation for Non-Newtonian liquids as described in Dynamics of Polymeric Liquids, Vol. 1, 1987 authored by R. B. Bird, R. C. Armstrong, and O. Hassager. The rate of deformation is given by a shear rate in a unit of $(time)^{-1}$. The viscosity measured at a known shear rate is "true" viscosity. The dependence of the true viscosity on shear rate is a viscosity curve which characterizes material and is an important factor to consider for efficient processing. But in many cases viscosity is measured under ill-defined test condition so that shear rate can not be known or calculated. Under ill-defined conditions, the measured viscosity value is only "apparent". Since the true viscosity is measured at a known shear rate, the true viscosity is universal whereas the apparent viscosity is not. Instead, the apparent viscosity depends on the measuring system. For example, as a common practice, a torque of a spindle immersed in a sea of test liquid is measured while the spindle is being rotated at a constant speed. In this case the torque value only yields an apparent viscosity since the shear rate is not known. At best, the apparent viscosity can be measured as a function of the rotational speed of the spindle. The rotational speed of the spindle can be in fact correlated with the shear rate only if a "constitutive equation" for the test liquid is known. However, a "constitutive equation" is seldom known for Non-Newtonian liquids. Therefore, true viscosity can not be measured with such ill-defined test condition for most non-Newtonian liquids.

The methods that give only apparent viscosities have been developed and used for quality controls in manufacturing and material characterization. Various on-line viscometers are designed for real time viscosity measurement. The prior art systems of U.S. Pat. No. 5,317,908 (Fitzgerald et al.) and U.S. Pat. No. 4,878,378 (Harada) are concerned with systems that measure apparent viscosities for process controls. The system of U.S. Pat. No. 6,393,898 describes a system that measures the apparent viscosities of many test liquids simultaneously. However, because of the non-universality of the apparent viscosity measurements obtained by these systems, a correlation of the apparent viscosity of a specific sample measured with a specific method with the true viscosity has to be found separately when desired. Fundamental development of formulations for materials requires the true viscosity measurement. Also the designs of processing equipment and accessories such as dies, molds, extrusion screws, etc., require the true viscosity of the material. However, the apparent viscosity measurement has been used for a quick test as an indication since it is easier and faster to measure and often more economical. The true viscosity is more difficult to get and can be only measured with a few types of instruments: rheometers and capillary viscometers. Rheometers impose a precise and known shear rate on test samples thereby measuring true viscosities. Rheometers are versatile and can be equipped to measure other properties also. Therefore they are usually expensive. Usually large amounts of sample are required for viscosity measurements with the prior art rheometers. Further, such rheometers are not well suited for on-line applications and for high throughput measurement. Circular capillary viscometers are another type of viscometer that can measure apparent and true viscosities depending on whether a proper compensation is taken into account. The capillary viscometer needs a pressure drop measurement along the capillary for viscosity. Since the capillary is circular, pressure at the entrance and exit can only be measured. Because of this limitation, the capillary viscometer measures only apparent viscosity unless the entrance effect is corrected for by using two different capillaries with different length to diameter ratios. However, use of two capillaries makes the viscometers bulky or time consuming. Examples of capillary viscometers can be found in prior art U.S. Pat. No. 6,575,019 (Larson), U.S. Pat. No. 4,920,787 (Dual et al.), U.S. Pat. No. 4,916,678 (Johnson et al.), and U.S. Pat. No. 4,793,174 (Yau).

Rectangular slit viscometers relevant to the current invention are also used to measure the true viscosity and such viscometers are well described in Rheology in Polymer Processing, 1976, authored by C. D. Han. In this viscometer, test liquid flows inside of a rectangular slit flow channel and local pressures along the flow channel are measured with deployed pressure sensors for a given flow rate. In contrast to the capillary viscometer, the inside of the slit flow channel is flat so that pressures in the slit flow channel can be measured with pressure sensors mounted in the slit flow channel. The positions of the pressure sensor have to be sufficiently inside of the slit flow channel so that pressures of a fully developed flow are measured. From the pressure measurement, wall shear stress can be calculated. As the flow rate is varied, shear rate can be varied. From the measurement of wall shear stress at different shear rates, true viscosities are calculated using the well known Weissenberg-Rabinowitsch correction, which is much simpler than using two separate capillaries in case of using circular capillary viscometers. These viscosity measurements, however, are only simpler if the width of the flow channel is sufficiently large compared to the depth of the flow channel. These slit viscometers need pumping systems for a precise control of volumetric flow rate of test liquid. Frequently, the slit viscometers are used as an attachment to extruders as the liquids flow out of the extruders. In current practices, the individual pressure sensors are mounted separately to the inside of the flow channels and must be mounted flush enough with the surface of the flow channel to measure unperturbed pressures. However, it is very well known that a perturbation of flow significantly influences pressure measurement in particular for viscoelastic non-Newtonian liquids. Also any slight surface roughness due to the mounting of pressure sensors may be a source of test sample deposition, which degrades long term performance let alone the difficulties of mounting individual pressure sensors. Therefore, the measurement accuracy is often compromised depending on how well the individual pressure sensors are mounted in the flow channel. With a single slit geometry, shear rate can only be changed by a change of volumetric flow rate controlled by the pumping system. Also, most current slit viscometers are made individually with conventional machining processes. In addition, all of these viscometers are made for relatively large samples. Therefore, relatively small sample sizes, such as micro sample sizes, cannot be measured with such systems. These conventional slit viscometers are not appropriate for measuring viscosities of test sample that are only available in a small quantity and for high throughput measurement.

For non-Newtonian liquids, flow elasticity is also a very important flow characteristic. The flow elasticity governs the flow in inkjetting, coating, spraying, etc. Therefore, measuring the flow elasticity is also an important characterization. Flow elasticity has been measured with rheometers, RFX opposed jet, Filament Stretching Extensional Rheometer (FISHER), Capillary Break-up Extensional Rheometer (CABER), Sudden Contraction flow Rheometers (Rodd, L. E., Scott, T. P., Boger, D. V., Cooper-White, J. J. and McKinley, G. H., Planar Entry Flow of Low Viscosity Elastic Fluids in Micro-Fabricated Geometries, *J. Non-Newt. Fluid Mech.* (2005), 129, 1-22), and converging flows rheometers (James, D. F., Flow in a Converging Channel at Moderate Reynolds Numbers, *AIChE J.*, 1991, 37, 59-64). All these instruments are fairly large in size and are not suitable for high throughput measurement applications. The micro-fabricated planar entry flow by Rodd et al. is promising as the planar geometry is compact. However, the material used for the flow channel is soft rubber and hard to combine with sensor substrates.

SUMMARY OF INVENTION

According to the invention, viscosity and various other flow characteristics of a very small or micro sample of flowable material can be determined using a rheometer having a micro slit flow channel with monolithically integrated pressure sensors. The micro flow channel is operable with very small sample sizes and the problem of rough areas on flow channel surfaces caused by placement of individual pressure sensors in the flow channel is overcome with pressure sensors monolithically integrated into the wall of a flow channel. Micro-fabrication processes such as used to make micro chips can advantageously be used in making such micro slit viscometers which allows these micro slit viscometers to be made in large quantity on a single wafer. The invention therefore makes these micro slit viscometers extremely cost-effective.

The micro-fluidic rheometers of the invention, sometimes referred to as a rheometer-on-a chip, has a micro flow passage with substantially smooth interior surfaces, one of which includes monolithic integrated pressure sensor arrays for sensing pressures along the micro-fabricated flow channel. A geometry change in the flow channel or passage forms a contraction region in the flow channel or passage. With proper placement of pressure sensors upstream and downstream of the contraction region, or in the contraction region, the extensional viscosity of the sample liquid can be measured.

In one embodiment of the invention, a flow channel is fabricated into a substantially rigid substrate such as glass or silicon with a monolithic pressure sensor array closing the top or the bottom of the channel to form the flow passage. The flow channel forms a substantially straight flow path with a sudden or gradual contraction and expansion in the flow path to simultaneously measure the viscosity and the pressure drop associated with the flow elasticity and viscosity as the streamlines of the test liquid experiences shearing, extension, and bending. In another embodiment of the invention, the flow passage is formed by two monolithic pressure sensor arrays sandwiching the flow channel through which the liquid flows. The two sets of pressure sensor arrays simultaneously measure the viscosity and the normal stresses. Multiple rheometers of the invention can be combined in parallel or in series with each other to measure flow properties of multiple samples in a high throughput manner. For high throughput measurement, automatic sample loading of many samples is added to the system. The auto sampled liquid is then pumped to the chip or chips for high throughput measurement.

A batch wafer micro-fabrication process to manufacture the rheometer-on-a-Chip is the currently preferred manufacturing method. This method of manufacture greatly reduces the production cost of the rheometers.

In a currently preferred embodiment of the invention, the rheometer-on-a-chip includes a flow cell and a pumping system capable of causing flow of a sample liquid through the rheometer flow passage in a controlled manner. The flow cell includes a micro-fabricated flow channel (or channels) with a micrometer order of depth for flow and with a monolithic pressure sensor arrays. Preferably the depth of the channel is greater than about 10 micrometer, the length of the channel is longer than about 300 micrometer, and the width is wider than about 100 micrometer. The flow channels are fabricated in a wafer in a known batch process. The monolithic pressure sensor arrays are also fabricated on a wafer or wafers. Examples of methods of fabrication of the flow channels and the pressure sensor arrays are described in my U.S. Pat. Nos. 6,892,583 and 7,290,441. The microfabricated wafer with many flow channels is combined with the microfabricated wafer with many monolithic pressure sensor arrays in a known manner. The combined wafer has many flow cells, which are further diced to separate individual rheometers-on-a-chip. The rheometers-on-a-chip so formed each form a slit viscometer, through which a test liquid is pumped to flow from one end of the flow channel to the other end of the flow channel and resulting pressure drops along the flow channel are measured.

A preferred method is to form the flow channel by etching wafers such as silicon (Si), Gallium Arsenide (GaAs), borosilicate (Pyrex 7740), or derivatives of these materials in a known manner.

A preferred fabrication method to form pressure sensors is to form a plurality of cavities on a plate so that the smooth measuring surface of the plate extends over the cavities to form an end of the cavity which will deform slightly in response to pressure applied to the smooth surface over the cavity. A single and simple detection mechanism is formed on each cavity to provide a measurement of pressure applied by the liquid under test against the surface over the cavity. The detection mechanism is capacitive, piezo-resistive, or optical.

The primary object of present invention is to provide a micro rheometer-on-a-Chip consisting of flow channels combined with one or two monolithic pressure sensor arrays to measure true viscosities and elasticities (apparent extensional viscosity and normal stress difference) with a miniscule amount of sample. Another objective of this invention is that the flow channels and pressure sensors are fabricated on wafers commonly used in microfabrication and they are combined in order to mass produce rheometers-on-a-chip in a cost effective manner.

THE DRAWINGS

The best mode presently contemplated for carrying out the invention is illustrated in the accompanying drawings, in which.

DETAILED DESCRIPTION OF THE ILLUSTRATED EMBODIMENT

Figure 1:
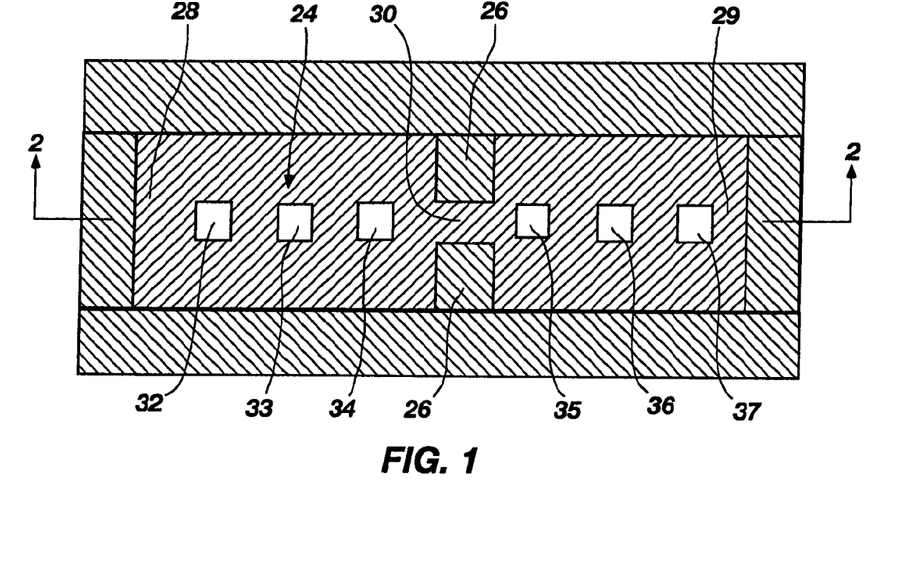
FIG. 1 is a horizontal section through a rheometer of the invention.
Figure 2:
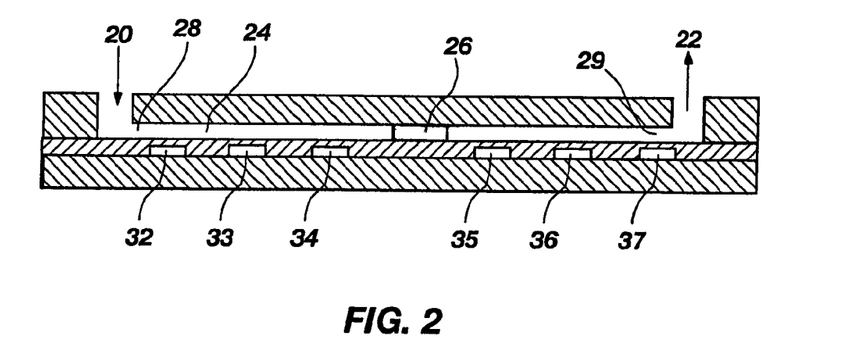
FIG. 2 is a vertical section taken on the line A-A through the rheometer of FIG. 1.
Figure 3A:
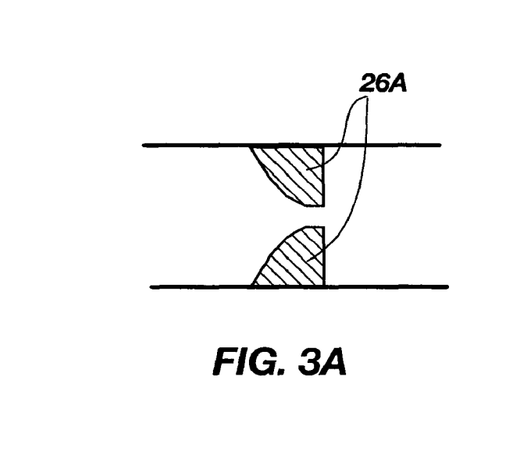
FIG. 3A-3E are top plan views of five possible alternative flow channel geometries.
Figure 3B:
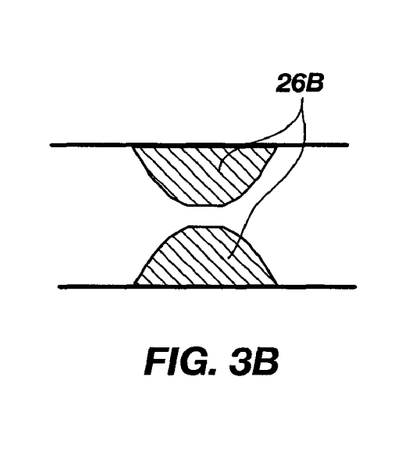
Figure 3C:
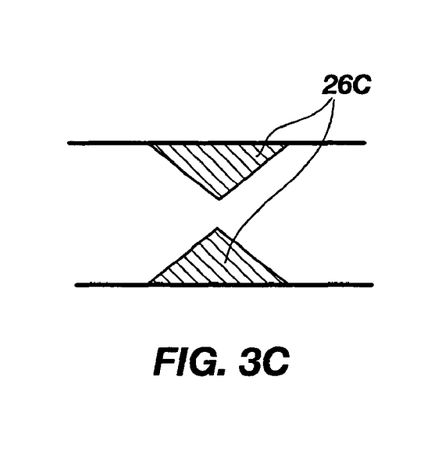
Figure 3D:
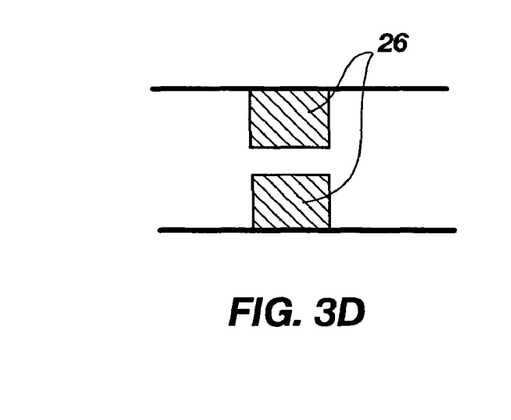

An embodiment of a micro rheometer-on-a-chip is shown in FIGS. 1 and 2 and includes a flow entrance or inlet 20, a flow exit or outlet 22, and a flow channel 24. The flow channel 24 has a predetermined channel depth (gap) in the order of micrometers along the channel and may have protrusions 26 in the intermediate portion, here shown as approximately the middle, of the length of the flow channel 24 to induce a contraction of flow of material flowing in the flow channel 24. The width of the flow channel is preferably significantly larger than the depth of the channel so that the flow through the channel can be considered to be a one-dimensional problem. The ratio of the width to the depth is preferably larger than ten. The preferred channel depth is in the order of micron. The preferred length of the channel is at least one hundred micrometers excluding the entrance and exit zones 28 and 29, respectively. In order to measure the true viscosity, the test liquid is pumped to flow through the channel at a known flow rate and at various flow rates. When there is a planar contraction flow, the shape of the contraction as formed by protrusions 26 can be rectangular as shown in FIGS. 1, 2, and 3D, hyperbolic contraction and sudden expansion as shown in FIG. 3A with protrusions 26A, hyperbolic contraction and hyperbolic expansion as shown in FIG. 3B with protrusions 26B, simple contraction and simple expansion as shown by the triangle protrusions 26C in FIG. 3C, and various other shapes of contractions formed by various other shapes of protrusions. These geometric changes induce planar extension of the liquid in the contraction region 30 in the region of the protrusions so that apparent extensional viscosity can be measured.

As shown in FIGS. 1 and 2, a pressure sensor array is arranged with pressure sensors 32, 33, 34, 35, 36, and 37 positioned along the flow channel 24. In order to minimize the flow disturbance in the flow channel and increase the measurement accuracy, the sensor array is made of a monolithic chip fabricated using chip micro-fabrication processes: MEMS (micro-electro-mechanical systems). In this way, the surface of the flow passage where the sensor array is located, i.e., the membrane covering and forming a part of the pressure sensors, is sufficiently smooth so as to not interfere with sample liquid flow. The membrane is preferably silicon. The flow channel can be formed in a borosilicate glass or other type of hard substrate. The process for forming the flow channel can be etching or thermal forming or thermal embossing. The preferred borosilicate glass is etched using HF etchant commonly employed in MEMS processes following the photolithography patterning of the photoresist coated over the glass surface. The patterned flow channel is then bonded with the monolithic sensor array in a known manner. More details of the pressure sensor arrays and examples of methods of fabrication of the flow channels and the pressure sensor arrays are described in my U.S. Pat. Nos. 6,892,583 and 7,290,441.

In operation, a syringe pump or positive displacement pump can be used to pump the sample liquid to be measured to the inlet port 20 of the flow channel 24. When the liquid flows through the flow channel or passage 24, the pressure sensors 32, 33, and 34 upstream of the contraction region measure the pressure drop directly related to the viscosity of the flowing sample. For this measurement, the sensors 32, 33, and 34 are sufficiently away from the entrance or inlet zone 28 and the contraction region 30 so that they measure the fully developed flow of sample. If pressure sensor 34 immediately upstream from the contraction region 30 is not sufficiently away from the contraction region so as not to be influenced by the contraction of the liquid flow passage, only sensors 32 and 33 will be used to determine the true viscosity. The sensors 35, 36, and 37 located in the uniform flow channel downstream of the contraction region can also be used to measure viscosity. Differences in viscosity measurements between the upstream sensors and the downstream sensors can indicated a problem with the viscosity measurements obtained.

Another useful measurement for liquids is a measurement of extensional viscosity. This is different from the viscosity measurement and is a measure based on the planar extension of the liquid in the contraction region 30. By measuring the difference in pressure drop between the sensor 34 immediately upstream of the contraction region 30 and the sensor 35 immediately downstream of the contraction region 30, the apparent extensional viscosity can be quantified.

Figure 3E:
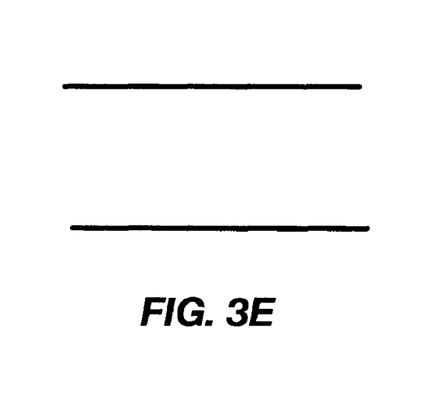

FIG. 3E shows a straight flow channel without a contraction. This type of channel is used when only true viscosity is to be measured.

Figure 4:
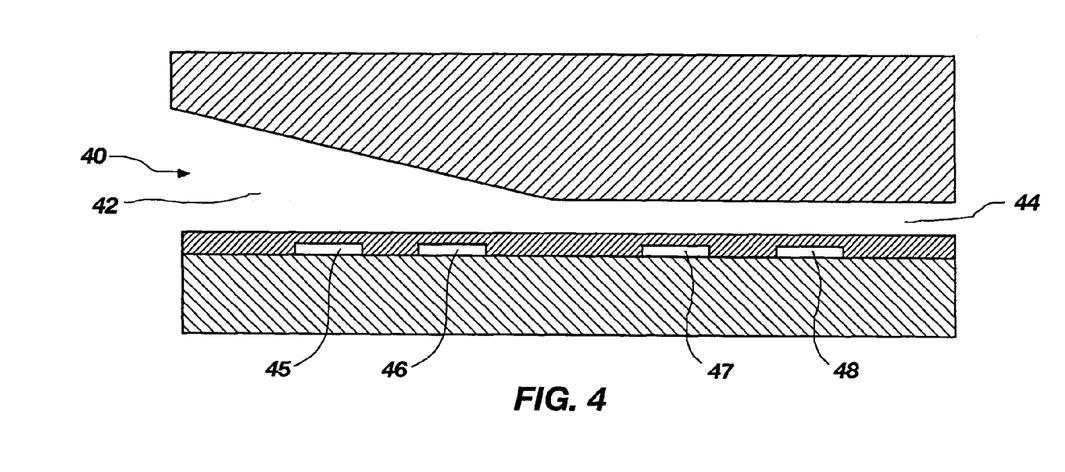
FIG. 4 is a vertical section showing a gradual contraction of a flow channel followed by a uniform channel gap.
Figure 5:
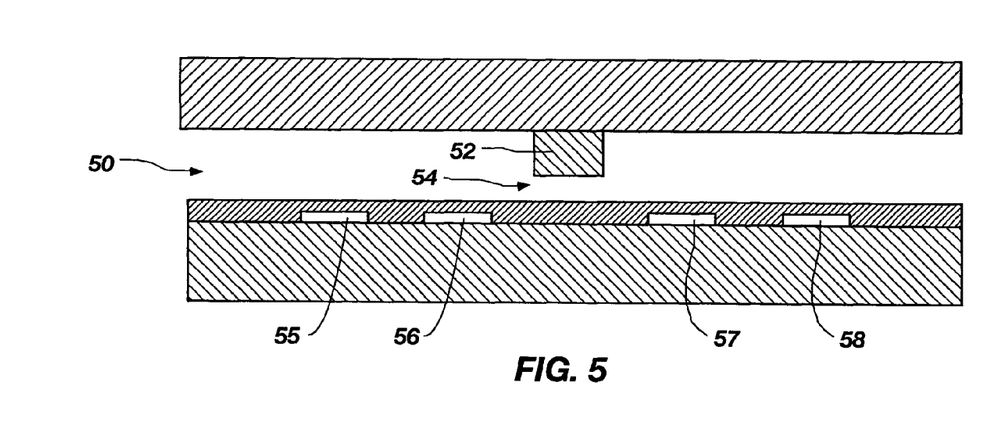
FIG. 5 is a vertical section of a sudden vertical contraction in the flow channel.

Alternative passage configurations for measuring viscosity, extensional viscosity, and elasticity is to employ the constructions shown in FIGS. 4 and 5. In FIG. 4, a flow channel 40 has a smooth continuously converging channel section 42 followed by a uniform flow channel section 44. The continuously converging flow channel is made in the substrate using thermal embossing. Pressure sensors 45 and 46 in the continuously converging channel section 42 measure the extensional viscosity and elasticity of the sample liquid, while the sensors 47 and 48 in the uniform flow channel section 44 measure the viscosity of the sample liquid. In FIG. 5, a uniform flow channel 50 has a sudden vertical contraction 52 which provides a contraction region 54 similar to the contraction region 30 in the embodiment of FIGS. 1 and 2. Sensors 55 and 56 in the upstream uniform portion of the flow channel 50 and sensors 57 and 58 in the downstream uniform portion of the flow channel 50 are used to measure viscosity, while the sensor 56 immediately upstream of the protrusion 52 and sensor 58 immediately downstream of protrusion 52 are used to measure the extensional viscosity, similarly to such measurement described for FIGS. 1 and 2.

Figure 6A:
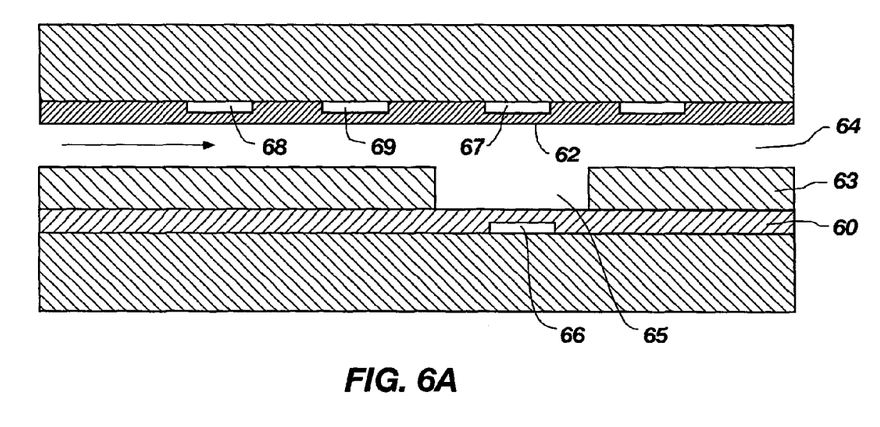
FIG. 6A is a vertical section through a rheometer of the invention which can measure and provide both viscosity and elasticity measurements.
Figure 6B:
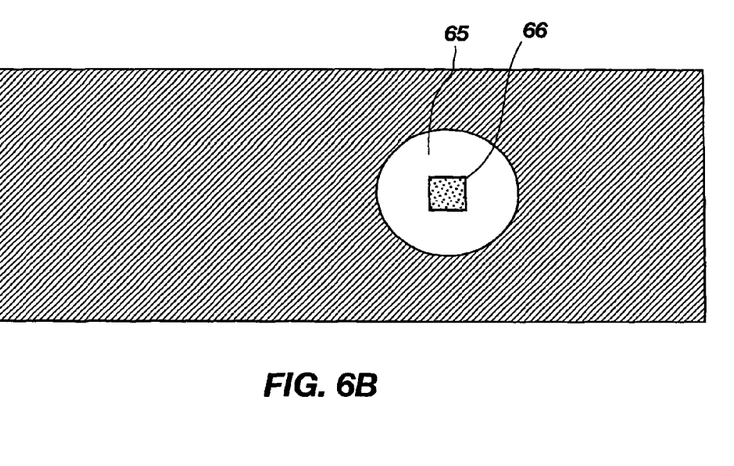
FIG. 6B is a horizontal section through the rheometer of FIG. 6A.
Figure 7:
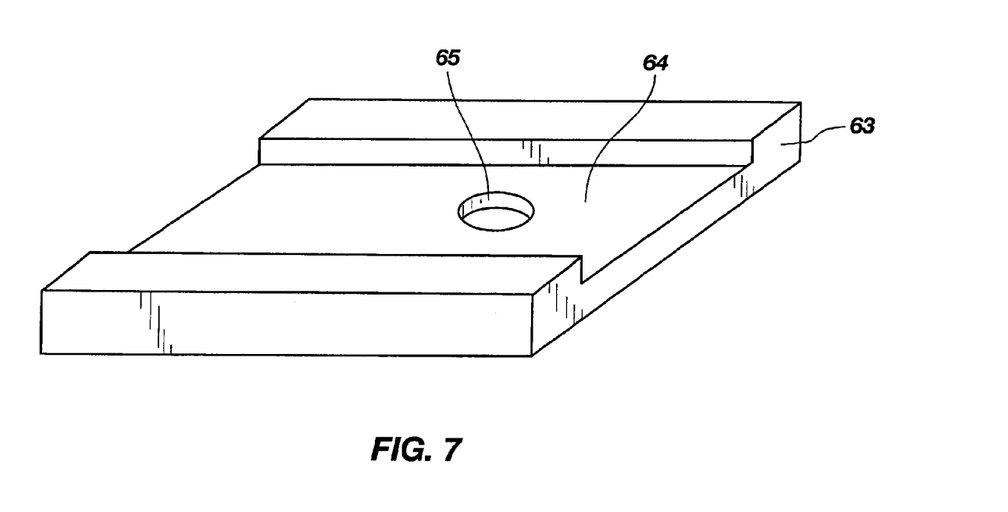
FIG. 7 is a fragmentary perspective view of the intermediate flow channel portion of the rheometer of FIG. 6.

Alternative passage configurations to measure viscosity and elasticity simultaneously can employ the design shown in FIGS. 6A and 6B. In this design, a bottom sensor array 60 and a top sensor array 62 sandwich a substrate 63 with middle flow channel 64, also shown in FIG. 7. As shown in the FIG. 7, there is a circular through hole 65 at the bottom of the middle flow channel 64. By measuring the pressure difference between the pressure sensor 66 below the circular hole 65 and the pressure sensor 67 directly above the circular hole 65, flow elasticity is calculated. By measuring the pressure drop of the leading pressure sensors 68 and 69, the viscosity is calculated. Therefore, the viscosity and elasticity can be calculated simultaneously.

These devices are constructed using microfabrication processes commonly used in chip fabrication. The preferred bonding of the monolithic sensor array (s) and the flow channel is air tight anodic bonding. Necessary lead transfers for electrical connections are made in a known manner to build a package chip.

Figure 8:
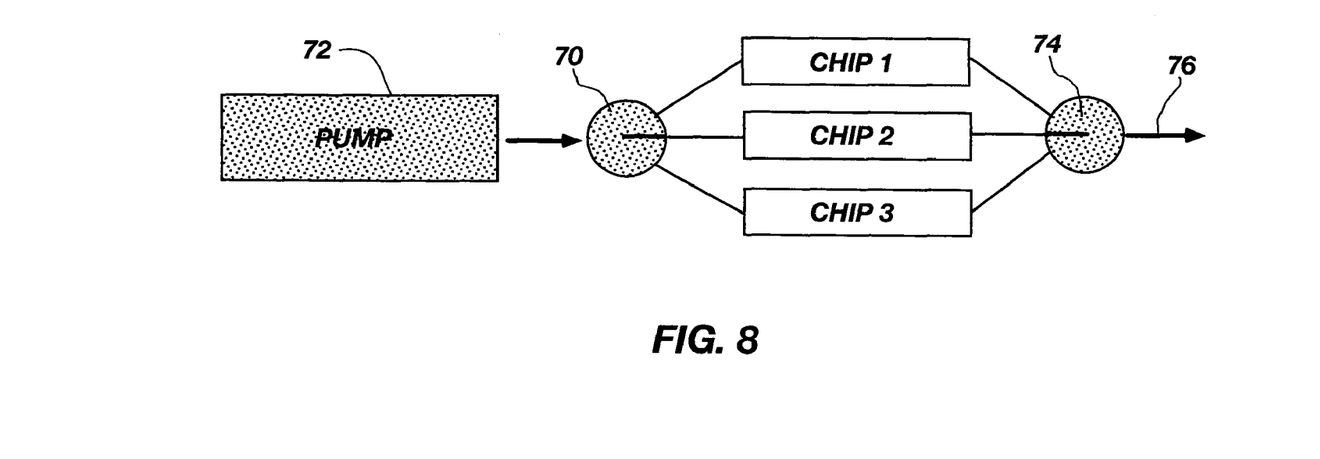
FIG. 8 is a schematic diagram of a chip array in parallel configuration.
Figure 9:
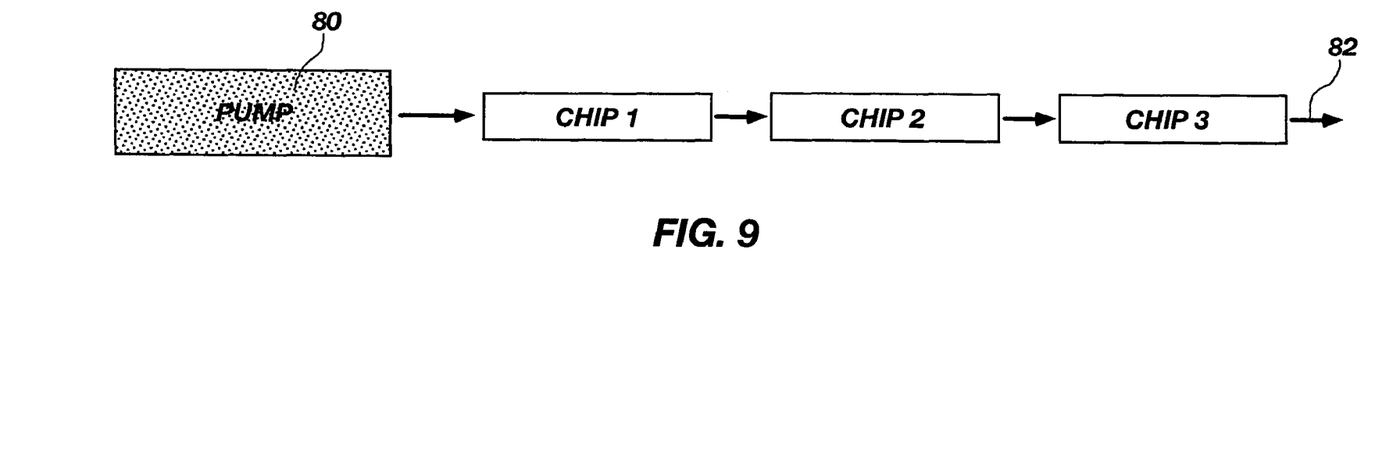
FIG. 9 is a schematic diagram of a chip array in series configuration.

Each packaged chip usually has a finite measurable range of viscosity or elasticity. In order to increase the measurable range several chips are arranged either in parallel as shown in FIG. 8, or in series as shown in FIG. 9. When the chips are arranged in parallel, the proper chips are chosen with a valve directing the liquid to flow through the chosen chip. Thus, as shown in FIG. 8, a valve 70 directs the liquid sample being pumped from pump 72 to either Chip 1, Chip 2, or Chip 3. The sample liquid flows through the rheometer on the selected Chip 1, Chip 2, or Chip 3 and back through valve 74 to a sample drain 76. When connected in series as shown in FIG. 9, pump 80 pumps the sample liquid through the chip rheometers Chip 1, Chip 2, and then Chip 3 from where the sample liquid discharges into sample drain 82.

With pumps, valves, appropriate displays, and the chips, a portable viscosity measurement system can be constructed in a known manner. The display can be a touch sensitive display. This viscosity measurement system can be arranged with a front end sampling system to pump the desired sample in a library of samples in a known manner. In this arrangement, the viscosity measurement can be performed automatically when the sampling system is programmed to pump the desired sample at known flow rates. If necessary, the whole sampling and device flow paths are cleaned with appropriate cleaning solutions between measurements. Such a controlled sampling system can be integrated with a proper sample selection station for fast and automatic sample viscosity measurement. Vast libraries of samples can be automatically selected with an auto-sampler. The selected sample is pumped to flow through the chip for viscosity measurement at one shear rate or at multiple shear rates. Based on pre-program criteria, the tested sample can be either accepted or rejected. The next sample is then selected and tested. This process continues automatically.

Figure 10:
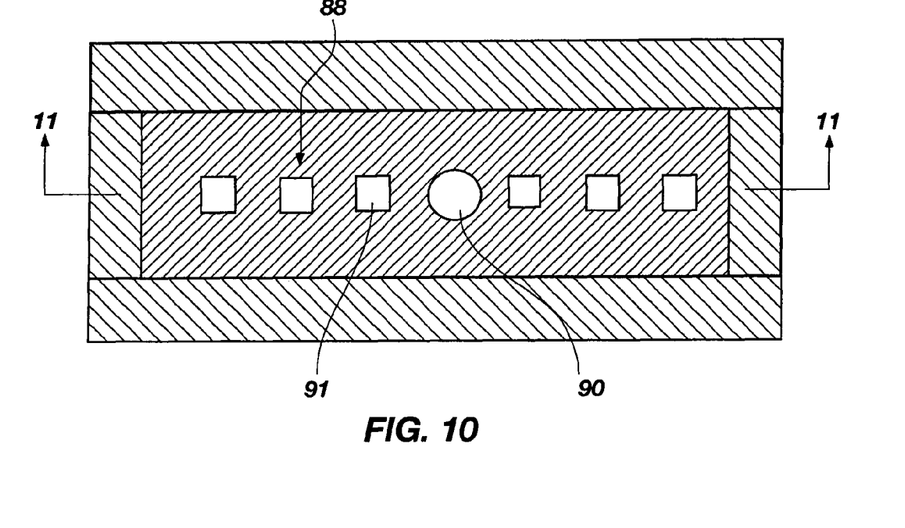
FIG. 10 is a horizontal section through a rheometer of the invention having a transparent flow channel for viewing samples while measuring viscosity and/or extensional viscosity or combination.
Figure 11:
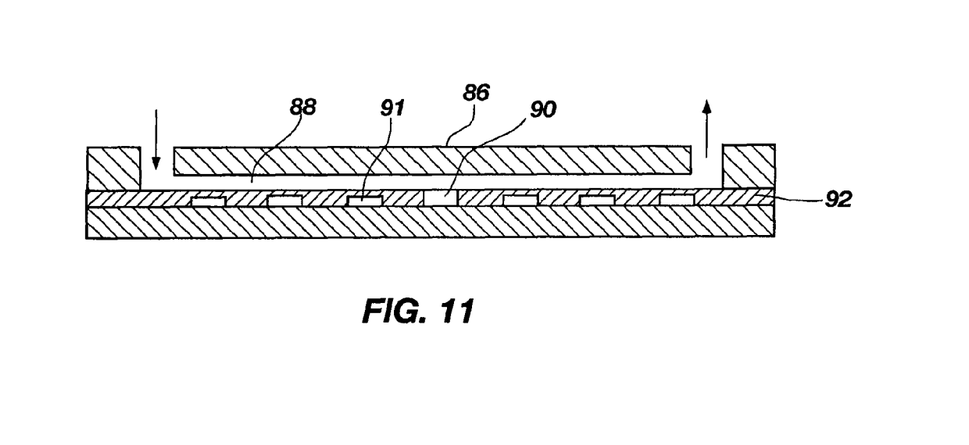
FIG. 11 is a vertical section taken on the line A-A through the rheometer of FIG. 10.

FIGS. 10 and 11 show another embodiment of a viscometer/rheometer-on-a-chip. In this embodiment, the viscometer/rheometer-on-a-chip can have a transparent substrate 86 forming flow channel 88 so that actual liquid flows in flow channel 88 can be visualized. A transparent hole 90 can also be provided. If a light transmission path is needed for the sensors, the sensor surface 91 of the pressure sensor array 92 will be made to be transparent or to have transparent sections so that light can pass through the transparent sections and the transparent flow channel substrate 86.

Figure 12A:
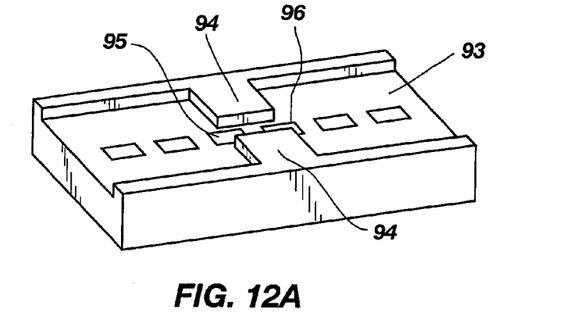
FIG. 12A-12C are perspective views of the intermediate flow channel portions of three alternative flow channel geometries.
Figure 12B:
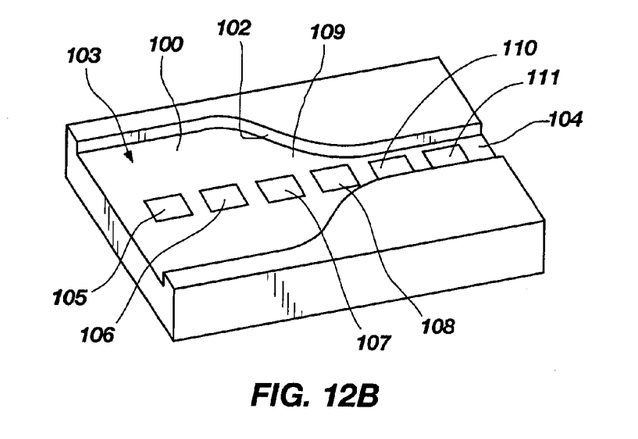
Figure 12C:
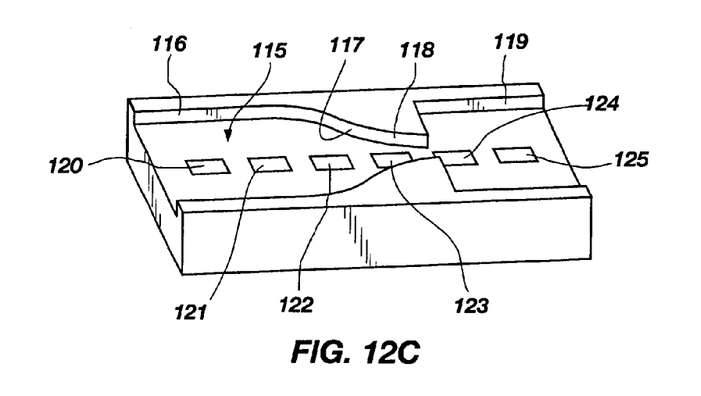

FIG. 12A shows a perspective view of the intermediate flow channel portion of a flow channel 93 having rectangular protrusions 94 forming a contraction of the flow channel, similar to the contraction of the flow channel of FIGS. 1 and 2. An alternate sensor array places pressure sensors 95 and 96 in the entrance and exit, respectively, of the contraction region. FIG. 12B shows a perspective view of the intermediate flow channel portion of a flow channel 100 having curved protrusions 102 forming a contraction of the flow channel from a large width section 103 to a smaller width section 104. A sensor array places pressure sensors 105 and 106 in the uniform large width section 103, sensors 107 and 108 in the narrowing contraction region 109, and sensors 110 and 111 in the uniform smaller width section 104. FIG. 12C shows a perspective view of the intermediate flow channel portion of a flow channel 115 having a uniform upstream section 116, curved protrusions 117 forming a contraction region 118, which expands suddenly to the same uniform width downstream portion 119 of the flow passage. A sensor array places pressure sensors 120 and 121 in the uniform upstream section 116, sensors 122 and 123 in the narrowing contraction region 118, and sensors 124 and 125 in the uniform same width downstream section 119.

If the viscosity of the sample test liquid is known a priori, then the chip rheometer can measure flow rate instead of viscosity.

The application has referred to measuring liquids. For purposes of this specification and claims, liquid refers to any flowable material that can be force to flow through the flow passages of the rheometer of the invention.

Whereas this invention is here illustrated and described with reference to embodiments thereof presently contemplated as the best mode of carrying out the invention in actual practice, it is to be realized that various changes may be made in adapting the invention to different embodiments without departing from the inventive concepts disclosed herein.

The invention claimed is:

1. A rheometer for measuring flow characteristics of a micro sample of liquid comprising:
   a substantially rigid flow channel having opposite ends with a sample inlet at one end and a sample outlet at the opposite end and having at least one geometry change along the channel which forms a contraction region in the flow channel;
   a plurality of pressure sensors located along the flow channel and positioned with respect to the at least one geometry change to measure a pressure of the sample exerted against the pressure sensors as a result of the geometry change;
   wherein said flow channel is formed by combining a hard substrate having an open three sided channel with a planar sensor array plate having monolithically integrated pressure sensors therein to close the open side of the three sided channel and position the sensors along the flow channel; and
   wherein the plurality of pressure sensors is at least two pressure sensors positioned in the contraction region whereby a measurement of a characteristic of the liquid sample related to the liquid sample behavior through the contraction region can be determined.

2. A rheometer for measuring flow characteristics of a micro sample of liquid according to claim 1, wherein the contraction region narrows the flow channel to a flow channel on the order of a micrometer.

3. A rheometer for measuring flow characteristics of a micro sample of liquid according to claim 1, wherein the geometry change is a gradual gap change followed by a uniform geometry portion of the flow passage.

4. A rheometer for measuring flow characteristics of a micro sample of liquid according to claim 1, additionally including a temperature sensor positioned with respect to the flow channel to measure the temperature of a sample in the flow channel.

5. A rheometer for measuring flow characteristics of a micro sample of liquid according to claim 1, wherein the characteristic of the sample liquid to be determined is the extensional viscosity.

6. A rheometer for measuring flow characteristics of a micro sample of liquid according to claim 1, wherein the at least two pressure sensors positioned in the contraction region is a pressure sensor positioned in the flow channel upstream of the geometry change to measure sample liquid pressure upstream of the geometry change and a pressure sensor positioned in the flow channel downstream of the geometry change to measure sample liquid pressure downstream of the geometry change whereby the measurement of a characteristic of the liquid sample related to the liquid sample behavior through the contraction region can be determined.

7. A rheometer for measuring flow characteristics of a micro sample of liquid according to claim 1, additionally including a sample fluid pump for pumping the sample fluid through the flow channel.

8. A rheometer for measuring flow characteristics of a micro sample of liquid comprising:
   a substantially rigid flow channel having opposite ends with a sample inlet at one end and a sample outlet at the opposite end and having at least one geometry change along the channel which forms a contraction region in the flow channel;
   a plurality of pressure sensors located along the flow channel and positioned with respect to the at least one geometry change to measure a pressure of the sample exerted against the pressure sensors as a result of the geometry change;
   wherein said flow channel is formed by combining a hard substrate having an open three sided channel with a planar sensor array plate having monolithically integrated pressure sensors therein to close the open side of the three sided channel and position the sensors along the flow channel;
   wherein pressure sensors of the plurality of pressure sensors are positioned in the flow channel with respect to the contraction region in the flow channel whereby a measurement of a characteristic of the liquid sample related to liquid sample behavior through the contraction region can be determined; and
   wherein the plurality of pressure sensors additionally include a plurality of pressure sensors located in a uniform geometry portion of the flow channel to measure pressure of the liquid during fully developed flow of the liquid in the uniform geometry portion of the flow passage whereby viscosity of the liquid can be determined.

9. A rheometer for measuring flow characteristics of a micro sample of liquid comprising:
   a substantially rigid flow channel having opposite ends with a sample inlet at one end and a sample outlet at the opposite end and having at least one geometry change along the channel;
   a plurality of pressure sensors located along the flow channel and positioned with respect to the at least one geometry change to measure a pressure of the sample exerted against the pressure sensors as a result of the geometry change;
   wherein said flow channel is formed by combining a hard substrate having an open three sided channel with a planar sensor array plate having monolithically integrated pressure sensors therein to close the open side of the three sided channel and position the sensors along the flow channel;
   a hole extending through the substrate opposite the open side of the channel;
   a pressure sensor sealing the hole through the substrate; and
   wherein the sensor array plate closing the open side of the channel positions a sensor opposite the sensor sealing the hole.

10. A rheometer for measuring flow characteristics of a micro sample of liquid according to claim 9, wherein the hole is non-circular.

11. A rheometer for measuring flow characteristics of a micro sample of liquid according to claim 9, wherein the geometry change forms a contraction region in the flow channel.

12. A rheometer for measuring flow characteristics of a micro sample of liquid according to claim 11, wherein pressure sensors of the plurality of pressure sensors are positioned in the flow channel with respect to the contraction region in the flow channel whereby a measurement of a characteristic of the liquid sample related to liquid sample behavior through the contraction region can be determined.

13. A rheometer for measuring flow characteristics of a micro sample of liquid according to claim 9, wherein the hole is circular.

14. A rheometer for measuring flow characteristics of a micro sample of liquid according to claim 9, wherein the pressure sensor sealing the hole is provided by a second pressure sensor array plate secured to the substrate to position a sensor of the second sensor array plate in the hole.

15. A rheometer for measuring flow characteristics of a micro sample of liquid comprising:
   a substantially rigid flow channel having opposite ends with a sample inlet at one end and a sample outlet at the opposite end and having at least one geometry change along the channel;
   a plurality of pressure sensors located along the flow channel and positioned with respect to the at least one geometry change to measure a pressure of the sample exerted against the pressure sensors as a result of the geometry change;
   wherein said flow channel is formed by combining a hard substrate having an open three sided channel with a planar sensor array plate having monolithically integrated pressure sensors therein to close the open side of the three sided channel and position the sensors along the flow channel; and
   wherein portions of the flow channel are transparent to allow the flow of liquid to be observed from outside the rheometer.

* * * * *